(12) United States Patent
Mohammed et al.

(10) Patent No.: US 12,630,586 B2
(45) Date of Patent: May 19, 2026

(54) PROCESS FOR THE PREPARATION OF PLECANATIDE

(71) Applicant: Auro Peptides Ltd., Hyderabad (IN)

(72) Inventors: Abdul Shafee Mohammed, Hyderabad (IN); Damodar Reddy Pakal, Hyderabad (IN); Bharti Deshmukh, Hyderabad (IN); Vivekananda Reddy Goli, Hyderabad (IN); Nagana Goud Agasaladinni, Hyderabad (IN)

(73) Assignee: Auro Peptides Ltd, Hyderabad (IN)

( * ) Notice: Subject to any disclaimer, the term of this patent is extended or adjusted under 35 U.S.C. 154(b) by 1082 days.

(21) Appl. No.: 17/617,709

(22) PCT Filed: Jun. 8, 2020

(86) PCT No.: PCT/IB2020/055350
§ 371 (c)(1),
(2) Date: Dec. 9, 2021

(87) PCT Pub. No.: WO2020/250102
PCT Pub. Date: Dec. 17, 2020

(65) Prior Publication Data
US 2022/0235096 A1 Jul. 28, 2022

(30) Foreign Application Priority Data
Jun. 10, 2019 (IN) .............................. 201941022914

(51) Int. Cl.
C07K 7/64 (2006.01)
C07K 1/02 (2006.01)
C07K 1/06 (2006.01)
C07K 1/16 (2006.01)

(52) U.S. Cl.
CPC ................ C07K 7/64 (2013.01); C07K 1/026 (2013.01); C07K 1/062 (2013.01); C07K 1/16 (2013.01)

(58) Field of Classification Search
CPC ............ C07K 7/08; C07K 7/64; A61K 38/10; A61K 38/12
See application file for complete search history.

(56) References Cited

U.S. PATENT DOCUMENTS

| | | | |
|---|---|---|---|
| 7,041,786 B2 | 5/2006 | Shailubhai et al. | |
| 9,580,471 B2 | 2/2017 | Bai et al. | |
| 2017/0240599 A1 * | 8/2017 | Vadlamani | ........... B01D 15/325 |

FOREIGN PATENT DOCUMENTS

| | | | |
|---|---|---|---|
| CN | 103694320 B | 11/2015 | |
| CN | 108003222 A | 5/2018 | |
| WO | WO2012118972 A2 * | 9/2012 | ............ C07K 14/47 |
| WO | WO2014197720 A2 * | 12/2014 | ............ C07K 14/81 |
| WO | 2018/205401 A1 | 11/2018 | |

OTHER PUBLICATIONS

Corradini et al. Epimerization of peptide nucleic acids analogs during solid-phase synthesis: optimization of the coupling conditions for increasinthe optical purity. J. Chem. Soc., Perkin Trans. 1, 2001, 2690-2696. (Year: 2001).*
Flegel et al. FMOC Deprotection By tert-Butylamlne And Its Comparison in Solution and Soud Phase Synthesis. Collection Symposium Series 2011 , 13, 41-44. (Year: 2011).*
Hackeng et al. Total chemical synthesis of human matrix Gla protein. Protein Science (2001), 10:864-870. (Year: 2001).*

* cited by examiner

*Primary Examiner* — Li N Komatsu
*Assistant Examiner* — Jia-Hai Lee
(74) *Attorney, Agent, or Firm* — Jay R Akhave; PatentScience LLC

(57) ABSTRACT
The present invention relates to a process for the preparation of Plecanatide, which comprises preparation of three fragments such as Fragment A (7 amino acids). Fragment B (3 amino acids). Fragment D (6 amino acids) and coupling the fragments to provide Plecanatide followed by purification using buffer system comprising Tris hydrochloride (or) Triethylammonium phosphate.

9 Claims, No Drawings

Specification includes a Sequence Listing.

PROCESS FOR THE PREPARATION OF PLECANATIDE

CROSS-REFERENCE TO RELATED APPLICATIONS

This application is a 371 of PCT/IB2020/0SS350 Jun. 8, 2020, which claims foreign priority of IN201941022914 filed on Jun. 10, 2019.

FIELD OF THE INVENTION

The present invention relates to a process for the preparation of Plecanatide, which comprises preparation of three Fragments such as Fragment A (7 amino acids), Fragment B (3 amino acids), Fragment D (6 amino acids) and coupling the Fragments to provide Plecanatide followed by purification using buffer system comprising Tris hydrochloride (or) Triethylammonium phosphate.

BACKGROUND OF THE INVENTION

Plecanatide is an agonist of the guanylate cyclase type-C receptor ("GCC agonists"). Plecanatide is a 16 amino acid peptide with the following chemical name: L-Leucine, L-asparaginyl-L-a-aspartyl-L-a-glutamyl-L-cysteinyl-L-α-glutamyl-L-leucyl-L-cysteinyl-L-valyl-L-asparaginyl-L-valyl-L-alanyl-L-cysteinyl-L-threonylglycyl-Lcysteinyl-, cyclic (4→12), (7→15)-bis(disulfide). The amino acid sequence for Plecanatide is shown below:

Formula I

Plecanatide is approved in the United States under the trade name TRULANCE™ for treatment of Chronic Idiopathic Constipation (CIC) in adult patients.

Plecanatide is described in U.S. Pat. No. 7,041,786. The US '786 patent discloses that the peptide including plecanatide are synthesized and purified (>95% purity) using a published procedure of Klodt, et al., J. Peptide Res. 50:222-230 (1997). The article discloses general solid-phase synthesis, deprotection of Fmoc groups with 20% piperidine in NMP, deprotection of dry peptidyl resins by using a mixture of TFA/EDT/H$_2$O, formation of disulfide bond by air oxidation and with iodine, acidification with TFA, purification using preparative C18-HPLC column (buffer A: 0.1% TFA, buffer B: 0.1% TFA in MeCN/water, 80:20).

US Patent No. U.S. Pat. No. 9,580,471 describes a process for preparation of plecanatide using combination of solid and solution phase synthesis. Further, US '471 describes purification process of peptide on RP-HPLC column followed by desalination by eluting column with aq. alcohol, concentration of obtained fractions and then precipitation with diethyl ether or MTBE to obtain Plecanatide.

The inventors of the present invention developed an improved process for the preparation of pure Plecanatide, which is simple, cost-effective, and avoids or reduces content of impurities and makes the process robust.

OBJECTIVE OF THE INVENTION

The objective of the present invention is to provide a process for the preparation of Plecanatide. Another objective of the present invention is to provide a process for the purification of Plecanatide.

SUMMARY OF THE INVENTION

In an aspect, the present invention provides a process for the preparation of Plecanatide of Formula I (SEQ ID NO 1):

Formula-I

3 which comprises the following steps:
a) coupling of Fragment A (SEQ ID NO 2) with Fragment B to provide Fragment C (SEQ ID NO 3);

Y-Cys(Z)-Val-Asn(Y)-Val-Ala-Cys(Z)-Thr(X)-OH   Fragment A (SEQ ID NO 2)

H-Gly-Cys(Z)-Lue(X)  Fragment B

H-Cys(Z)-Val-Asn(Y)-Val-Ala-Cys(Z)-Thr(X)-Gly-Cys(Z)-Lue(X)  Fragment C (SEQ ID NO 3)

b) coupling of the Fragment C (SEQ ID NO 3) with Fragment D (SEQ ID NO 4):

```
                                      (SEQ ID NO 4)
Y-Asn(Y)-Asp(X)-Glu(X)-Cys(Z)-Glu(X)-Lue-OH
Faragment D
``` to provide protected linear peptide (SEQ ID NO 5);

```
                                      (SEQ ID NO 5)
H-Asn(Y)-Asp(X)-Glu(X)-Cys(Z)-Glu(X)-Lue-Cys(Z)-

Val-Asn(Y)-Val-Ala-Cys(Z)-Thr(X)-Gly-Cys(Z)-

Lue(X)

Protected linear peptide
``` c) deprotecting protected linear peptide to obtain linear 1-16 peptide (SEQ ID NO 6); and

```
                                      (SEQ ID NO 6)
H-Asn-Asp-Glu-Cys-Glu-Lue-Cys(Z)-Val-Asn-Val-Ala-

Cys-Thr-Gly-Cys(Z)-Lue-OH 1-16 linear peptide
``` d) oxidizing the linear 1-16 peptide to obtain Plecanatide.
In another aspect, the present invention provides a process for the purification of Plecanatide, which comprises:
a) purification on preparative HPLC column with Tris hydrochloride (buffer A) and acetonitrile (buffer B) to obtain Plecanatide having purity >95%;
b) second purification of Plecanatide obtained from step a) on preparative HPLC column with Tris hydrochloride (buffer A) and acetonitrile (buffer B) to obtain pure Plecanatide (>99%); or
c) purification of Plecanatide obtained from step a) on preparative HPLC column with Triethylammonium phosphate (buffer A) and acetonitrile (buffer B) to obtain pure Plecanatide (>99%);
d) desalting of Plecanatide obtained from step b) or step c) on preparative HPLC column with acetic acid in water and acetonitrile; and
e) isolation of pure Plecanatide.

4

BRIEF DESCRIPTION OF ABBREVIATIONS AND DEFINITIONS

DCC: N,N'-Dicyclohexylcarbodiimide
Dcb: 2,6-Dichlorobenzyl
Cbz: Carboxybenzyl
CTC: Chlorotrityl chloride
Boc: t-Butyloxycarbonyl
DIPEA: Diisopropylethylamine
HOBT: Hydroxy Benzotriazole
OtBu: O-t-Butyl
Xan: 9-Xanthenyl
DIC: Diisopropylcarbodiimide
DTT: Dithiothreitol
IBCF: Iso-butylchloroformate
IPCF: Isopropyl chloroformate
TIPS/TIS: Triisopropylsilane
HOSu: N-Hydroxysuccinimide
HOAt: 7-Aza-1-hydroxybenzotriazole Tris HCl: 2-Amino-2-(hydroxymethyl)-1,3-propanediol hydrochloride
HBTU: O-(Benzotriazol-1-0)-1,1,3,3-tetramethyluronium hexafluorophosphate
BOP: Benzotriazole-1-yl-oxytris(dimethylamino) phosphonium hexafluorophosphate
HATU: O-(7-Azabenzotriazol-1-yl)-1,1,3,3-tetramethyluronium hexafluorophosphate
Oxyma: Ethyl-2-cyano-2-(hydroxyimino)acetate
Fmoc: Fluorenylmethyloxycarbonyl
TBTU: O-(Benzotriazol-1-yl)-N,N,N',N'-tetramethyluronium tetrafluoroborate
SPPS: Solid phase peptide synthesis
PyBrOP: Bromo-tris-pyrrolidino-phosphonium hexafluorophosphate
BOP—Cl: N,N-Bis-(2-oxo-3-oxazolidinyl)phosphonic dichloride
WSCDI: 1-(Dimethylaminopropyl)-3-ethylcarbodiimide hydrochloride
TNTU: 2-(5-Norbornen-2,3-dicarboximido)-1,1,3,3-tetramethyluronium tetrafluoroborate
EEDQ: N-Ethoxycarbonyl-2-ethoxy-1,2-dihydroquinoline
PPAA: Propane phosphonic acid anhydride
TSTU: 2-Succinimido-1,1,3,3-tetramethyluronium tetrafluoro borate
HODhbt: 1-Oxo-2-hydroxy dihydrobenzotriazine

DETAILED DESCRIPTION OF THE INVENTION

The present invention relates to a process for the preparation of Plecanatide by coupling of two or more protected fragments either by solution phase or SPPS methods.

In an aspect, the present invention provides a process for the preparation of Plecanatide of Formula I (SEQ ID NO 1):

Formula-I

H-Asn-Asp-Glu-Cys-Glu-Leu-Cys-Val-Asn-Val-Ala-Cys-Thr-Gly-Cys-Leu-OH which comprises the following steps:

a) coupling of Fragment A (SEQ ID NO 2) with Fragment B to provide Fragment C (SEQ ID NO 3);

Y-Cys(Z)-Val-Asn(Y)-Val-Ala-Cys(Z)-Thr(X)-OH   Fragment A (SEQ ID NO 2)

H-Gly-Cys(Z)-Lue(X)   Fragment B

H-Cys(Z)-Val-Asn(Y)-Val-Ala-Cys(Z)-Thr(X)-Gly-Cys(Z)-Lue(X)   Fragment C (SEQ ID NO 3)

b) coupling of the Fragment C (SEQ ID NO 3) with Fragment D (SEQ ID NO 4):

```
                                        (SEQ ID NO 4)
  Y-Asn(Y)-Asp(X)-Glu(X)-Cys(Z)-Glu(X)-Lue-OH
  Faragment D
``` to provide protected linear peptide (SEQ ID NO 5);

```
                                        (SEQ ID NO 5)
H-Asn(Y)-Asp(X)-Glu(X)-Cys(Z)-Glu(X)-Lue-Cys(Z)-

Val-Asn(Y)-Val-Ala-Cys(Z)-Thr(X)-Gly-Cys(Z)-

Lue(X)

Protected linear peptide
``` c) deprotecting the protected linear peptide to obtain linear 1-16 peptide (SEQ ID NO 6); and

```
                                        (SEQ ID NO 6)
H-Asn-Asp-Glu-Cys-Glu-Lue-Cys(Z)-Val-Asn-Val-Ala-

Cys-Thr-Gly-Cys(Z)-Lue-OH 1-16 linear peptide
``` d) oxidizing the linear 1-16 peptide to obtain Plecanatide, wherein Y represents amino protecting group, X represents carboxyl, phenol and alcoholic protecting group, Z-represents thiol protecting group.

The side chain protecting groups for a hydroxyl group in an amino acid include, but are not limited to, benzyl (Bzl), tert-butyl (tBu), acetamidomethyl (Acm), and trityl (Trt), tetrahydropyranyl, Cbz, and 2,5-dichlorobenzyl (Dcb). The suitable side chain protecting groups for a thiol group include, but are not limited to, acetamidomethyl (Acm), trityl (Trt), Bzl, tBu, tert-butylthio (tButhio), p-methoxybenzyl (pMeoBzl), and 4-methoxytrityl (Mmt). The side chain protecting groups for a carboxylic acid include, but are not limited to benzyl, 2,6-dichlorobenzyl, tBu, and cyclohexyl. The side chain protecting groups for amide group include, but are not limited to, Xan, Trt; and the side chain protecting groups for alpha amino protecting group include, but are not limited to Fmoc.

In an embodiment, the Fragment A (SEQ ID NO 2) and Fragment D (SEQ ID NO 4) are prepared in solid phase synthesis; Fragment-B is prepared in solution phase; and coupling of the fragments is performed in solution phase.

The solid phase synthesis comprises elongation of peptide sequence by coupling of protected amino acids onto a peptide resin, cleaving amino protecting group, coupling of second protected amino acid via peptide linkage to the carboxyl group of a second protected amino acid and repeating the cycle till to obtain protected peptide intermediates. The resin is selected from the followings: wang resin, TentaGel S, chlorotrityl resin (CTC), 4-methytrityl chloride resin, TentaGel TGA, Rink acid resin, NovaSyn TGT resin, HMPB-AM resin.

The process for the preparation of linear 1-16 peptide involves coupling of Fragment A (SEQ ID NO 2) (7 amino acids) with Fragment B (3 amino acid) in solution phase in the presence of a coupling reagent to produce a Fmoc-protected Decapeptide (Fragment C) (SEQ ID NO 3), which is subjected for Fmoc deprotection in the presence of base to produce a decapeptide. The obtained decapeptide is coupled with a Fragment D (SEQ ID NO 4) (6 amino acids) by solution phase in presence of a coupling agent to give a protected linear 1-16 peptide (SEQ ID NO 5), which is then deprotected with a cocktail mixture to produce linear 1-16 peptide (SEQ ID NO 6).

In an embodiment, the Fragment A (SEQ ID NO 2) is Fmoc-Cys(Acm)-Val-Asn(Trt)-Val-Ala-Cys(Trt)-Thr(tBu)-OH, the Fragment B is H-Gly-Cys(Acm)-Leu-OtBu, the Fragment C (SEQ ID NO 3) is H-Cys(Acm)-Val-Asn(Trt)-Val-Ala-Cys(Trt)-Thr(tBu)-Gly-Cys(Acm)-Leu-OtBu and the Fragment D (SEQ ID NO 4) is Boc-Asn(Xan)-Asp(OtBu)-Glu(OtBu)-Cys(Trt)-Glu(OtBu)-Leu-OH.

The coupling reagent is used in presence or absence of additive. The coupling reagents includes but are not limited to DIC, DCC, HATU, HBTU, TBTU, BOP, BOP-CI, PyBOP, PyBrOP, IBCF, WSCDI, EEDQ, IPCF, TNTU, PPAA, TSTU, PyCIOP, Oxyma pure, TCTU, COMU, HOSu, The additive includes but are not limited to HOBt, HODhbt, HOAt, 6-CF$_3$-HOBt 6-NO$_2$-HOBt, Oxyma or mixture thereof. In one embodiment, the coupling agent and additive is of HATU/HOAt.

The base used for coupling is an organic or inorganic base. The inorganic base comprises potassium carbonate, lithium carbonate, sodium carbonate, sodium bicarbonate, potassium bicarbonate, sodium hydroxide, potassium hydroxide, ammonium hydroxide, and mixtures thereof; the organic base comprises t-butylamine, 4-Dimethylaminopyridine (DMAP), diisopropylamine, DIPEA, triethylamine, dimethylamine, trimethyl amine, isopropyl ethylamine, pyridine, N-methyl morpholine, piperidine, 1,8-diazabicyclo[5.4.0]undec-7-ene (DBU), and/or mixtures thereof. The solvent may be used for coupling reaction that comprises dimethylformamide (DMF), dimethylsulfoxide (DMSO), N-Methyl pyrrolidine (NMP), Dimethylacetamide (DMAC), dichloromethane (DCM), methanol, isopropanol, dichloroethane, 1,4-dioxane, tetrahydrofuran (THF), 2-methyl tetrahydrofuran, ethyl acetate, acetonitrile, acetone or mixtures thereof.

The base used for Fmoc deprotection includes but are not limited to t-butylamine, piperidine, diethyl amine, DBU, piperazine, pyrrolidine, derivatives of piperadine, piperazine and pyrrolidine in presence of solvent comprises alcohol, amide or ether. In one embodiment, the base and solvent used for Fmoc deprotection are t-butylamine and DMF.

In an embodiment, the cleavage and deblocking is performed in presence of cocktail mixture i.e. TFA: TIPS: DTT: solvent (or) TFA: TIPS: DTT: water: solvent (or) TFA: TIS: solvent. The solvent comprises water, dimethyl sulfide (DMS), alcohol solvent selected form methanol, ethanol, 1-propanaol, isopropanol, n-butanol; chlorinated solvent is selected form dichloromethane, dichloroethane, chlorobenzene; ether solvent selected form diethyl ester, THF, diisopropylether and/or combination thereof. The additional cocktail reagents is selected from 1,2-ethanedithiol (EDT), DMS, thioanisole, phenol, anisole etc. In an embodiment, the present invention provides deblocking of protected linear peptide using a mixture of TFA: TIPS: DTT: water: DMS.

In one embodiment, the cleavage and deblocking is performed in presence of cocktail mixture is Cocktail of 84% TFA (Trifluoroacetic acid): 5% TIPS (Triisopropylsilane): 5% $H_2O$: (5% DTT (Dithiothreitol) or 5% DMS.

After completion of cleavage and deprotection, the linear peptide or its TFA salt is precipitated by using suitable solvent, which is selected from ether solvent like diethyl ether, diisopropyl ether, methyl tertiary butyl ether, ethyl acetate and tetrahydrofuran.

After completion of cleavage and deprotection, the linear peptide is oxidized with molecular oxygen and/or oxidizing agent comprises hydrogen peroxide, dimethyl sulfoxide in presence or absence of solvent, which is selected from water, nitrile, alcoholic solvent or combination thereof. The obtained peptide optionally treated with Iodine in a solvent, which is selected from nitrile to provide dicyclised peptide. The oxidation may be performed at a pH range from 3 to 4.

The oxidation of open-chain peptide containing two free and/or two protected sulfhydryl groups with hydrogen peroxide. The protected/non-protected linear peptide may be subjected for pH adjustment of 3 to 4 or 6 to 7 by using acid/base followed by air oxidation using hydrogen peroxide and compressed air to afford mono-cyclized 1-16 peptide. The mono-cyclized peptide may be further treated with iodine in a solvent comprising nitrile solvent to provide disulfide 1-16 peptide i.e. Plecanatide.

In another embodiment, the present invention provides a process for the preparation of Fragment A (SEQ ID NO 2) is shown in the below Scheme-1.

Scheme-1

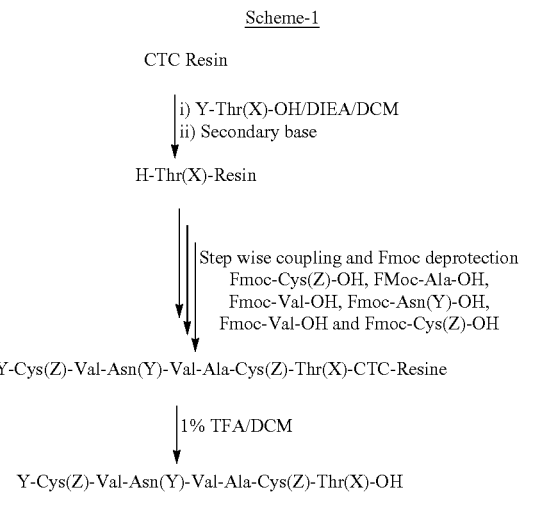

CTC Resin i) Y-Thr(X)-OH/DIEA/DCM
ii) Secondary base

H-Thr(X)-Resin

Step wise coupling and Fmoc deprotection
Fmoc-Cys(Z)-OH, FMoc-Ala-OH,
Fmoc-Val-OH, Fmoc-Asn(Y)-OH,
Fmoc-Val-OH and Fmoc-Cys(Z)-OH Y-Cys(Z)-Val-Asn(Y)-Val-Ala-Cys(Z)-Thr(X)-CTC-Resine

1% TFA/DCM

Y-Cys(Z)-Val-Asn(Y)-Val-Ala-Cys(Z)-Thr(X)-OH

In yet another embodiment, the present invention provides a process for the preparation of Fragment B is shown in the below Scheme-2.

Scheme-2

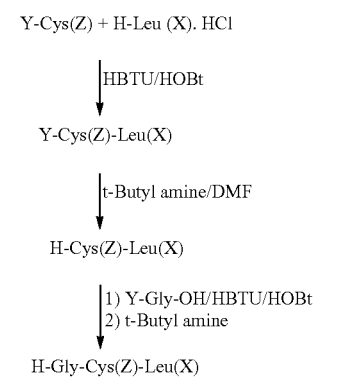

Y-Cys(Z) + H-Leu (X). HCl

HBTU/HOBt

Y-Cys(Z)-Leu(X)

t-Butyl amine/DMF

H-Cys(Z)-Leu(X)

1) Y-Gly-OH/HBTU/HOBt
2) t-Butyl amine

H-Gly-Cys(Z)-Leu(X)

In yet another embodiment, the present invention provides a process for the process for the preparation of Fragment D (SEQ ID NO 4) is shown in the below Scheme-3.

Scheme-3

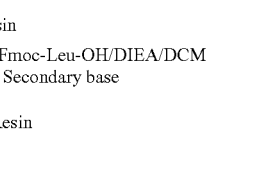

CTC Resin i) Fmoc-Leu-OH/DIEA/DCM
ii) Secondary base

H-Leu-Resin

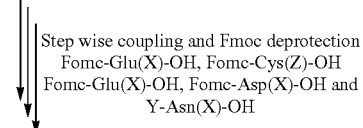

Step wise coupling and Fmoc deprotection
Fomc-Glu(X)-OH, Fomc-Cys(Z)-OH
Fomc-Glu(X)-OH, Fomc-Asp(X)-OH and
Y-Asn(X)-OH Y-Asn(Y)-Asp(X)-Glu(X)-Cys(Z)-Glu (X) -Leu-CTCResin 1% TFA in DCM Y-Asn(Y)-Asp(X)-Glu(X)-Cys(Z)-Glu (X) -Leu-OH The crude Plecanatide obtained by the process of present invention can be purified using preparative column chromatography or reverse phase column chromatography (RPHPLC).

In another aspect of the present invention, there is provided a process for the purification of Plecanatide of Formula I, which comprises:

a) purification on preparative HPLC column with Tris hydrochloride (buffer A) and acetonitrile (buffer B) to obtain Plecanatide having purity>95%;

b) second purification of Plecanatide obtained from step a) on preparative HPLC column with Tris hydrochloride (buffer A) and acetonitrile (buffer B) to obtain pure Plecanatide (>99%); or c) purification of Plecanatide obtained from step a) on preparative HPLC column with Triethylammonium phosphate (buffer A) and acetonitrile (buffer B) to obtain pure Plecanatide (>99%);

d) desalting of Plecanatide obtained from step b) or step c) on preparative HPLC column with acetic acid in water and acetonitrile; and e) isolation of pure Plecanatide.

The present application relates to a purification process of crude Plecanatide or a reaction mixture containing Plecanatide comprising preparative reverse phase column chromatography. The column in preparative HPLC may be packed with reverse phase C18 hydrid silica. Suitable silica gel types, which can be selected from, but are not limited to the following silica gel sorbents: Kromasil™MC18 100-16, Kromasil™C18 100-10, Kromasil™C8 100-16, Kromasil™C4 100-16, Kromasil™ Phenyl 100-10, Kromasil™ CI 8 Eternity 100-5, Kromasil™ C4 Eternity 100-5, Chromatorex™ CI 8 SMB 100-15 HE, Chromatorex™ C8 SMB 100-15 HE, Chromatorex™ C4 SMB 100-15 HE, Daisopak™ SP 120-15 ODS-AP, Daisopak™ SP 120-10-C4-Bio, Daisopak™ SP 200-10-C4-Bio, Zeosphere™ C18 100-15, Zeosphere™ C8 100-15, Zeosphere™ C4 100-15, SepTech ST 150-10 C18, Luna C18 100-10, Gemini C18 110-10, YMC Triart C18 120-5 and YMC Triart C8 200-10.

The column is packed with silica using Tris HCl having pH of 6 to 8 or pH of 7 and nitrile solvent such as acetonitrile, as buffers to obtain fractions having purity of about 94% by HPLC. The obtained fractions may be re-purified using column by packing with reverse phase C18 hybrid silica using Tris HCl.

The Plecanatide obtained according to the present invention has purity greater than 95% and preferably greater than 99% (by HPLC). The yields of the Plecanatide obtained according to present invention are consistent.

The Plecanatide, as produced by any one of the reaction conditions and purification process described above, undergoes desalting process by ion-exchange/preparative column chromatography. The resultant pure Plecanatide is subjected for precipitation, lyophilization or spray drying techniques to provide amorphous or crystalline Plecanatide.

Having described the invention with reference to certain aspects and embodiments, which will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1: Synthesis of
H-Gly-Cys(Acm)-Leu-Otbu (Fragment B)

Step-I: Synthesis of H-Cys(Acm)-Lue-Otbu

H-Leu-(Otbu). HCl (356.27 gm, 1.1 eq), HOBT (222.97 gm,1.0 eq) were added to a solution of Fmoc-Cys(Acm)-OH (600.0 g, 1.0 eq) in DMF (3.0 L) and then cooled to 5-10° C. HBTU (603.9 gm, 1.1 eq) and DIPEA (883.4 ml, 3.5 eq) were added to the reaction mass. After completion of the reaction, the product was extracted with ethyl acetate (6.0 L) and then washed with HCl, 5% aq sodium bicarbonate soln, 10% NaCl solution and water. The organic layer was collected, filtered and the filtrate was concentrated to obtain Fmoc-protected dipeptide. The obtained product was proceeded for next step without any further purification. Yield: 945 g Fmoc-Cys(Acm)-Leu-Otbu (945 g, 1 eq) was taken in flask containing DMF (1.89 L) and cooled the solution to 5-10° C. Tertiary butyl amine (255 ml 1.5 eq) was added slowly to the solution and stirred for 15 min. After completion of reaction, the reaction mass was cooled to 5-10° C. Water and IN HCl were added to the solution and the obtained aqueous solution was washed with hexane. The pH of product was adjusted to 8 to 8.5 with saturated sodium bicarbonate solution and the product was extracted with ethyl acetate. The ethyl acetate layer was washed with 10% NaCl solution and water and then filtered. The obtained filtrate was evaporated completely to obtained light yellow thick residue H-Cys(Acm)-Leu-Otbu. Yield: 450 g.

Step-II: Synthesis of H-Gly-Cys(Acm)-Lue-Otbu

H-Cys(Acm)-Leu-Otbu (450.0 g, 1.1 eq) was taken in flask containing DMF (1.68 L). Fmoc-Gly-OH (336.45 g, 1.0 eq), HOBT (174.2 g, 1.0 eq) were added to the solution and then cooled to 5-10° C. HBTU (472 g, 1.1 eq) and DIPEA (414.15 ml, 2.1 eq) were added and stirred. After completion of the reaction, ethyl acetate was added to the above reaction mass and washed with pre-cooled 0.5N HCl, 5% aqueous NaHCO₃ solution (pre-cooled), 10% NaCl solution and water. The resultant organic layer was evaporated completely to give Fmoc-Gly-Cys(Acm)-Leu-Otbu. Yield: 825 g.

Fmoc-Gly-Cys(Acm)-Leu-Otbu (825 g, 1 eq) was taken in flask containing THF (1650 ml) and cooled to 5-10° C. Tertiary butyl amine (338 ml 2.5 eq) was added slowly to the solution. After completion of reaction, the solution was cooled to 5-10° C. and then water (2.48 L) was added to the reaction mass. The aqueous reaction mass was washed with hexane, 50% ethyl acetate in hexane, then the product was extracted with dichloromethane. The dichloromethane layer was washed with 10% NaCl solution and water. The (collected) organic layer was dried with anhydrous sodium sulphate and then filtered. The obtained filtrate was evaporated completely to obtain H-Gly-Cys(Acm)-Leu-Otbu as light yellow semi solid. Yield: 392 g; HPLC purity: ~ 92%.

Example 2: Fmoc-Cys(Acm)-Val-Asn(Trt)-Val-Ala-Cys(Trt)-Thr(Otbu)-2CTC. (Fragment-A) (SEQ ID NO 2)

Step A: CTC resin (750 gm) was taken in a SPPS reactor, 7.5 L of dry dichloromethane (DCM) was added and allowed it to swell for 20 min and drained. Step B: A solution of Fmoc-Thr(otbu)-OH (954 gm, 2 eq) and DIEA (627.6 ml, 3 eq) in dry dichloromethane (3.75 L) were added to the resin at step A and stirred for at room temperature and drained. The resin was then capped with DIEA (1%) solution in DCM: methanol (1:1)) and then drained. Thereafter, washed the resin with one bed volume of DMF (2 times), DCM (2 times) and MTBE (2 times), isolated and dried. Yield: 1150 gm The above resin was deblocked with 20% piperidine in DMF and washed with DMF (2 times), IPA (2 times) and DMF (2 times).

Step C: To a solution of Fmoc-Cys(Trt)-OH (808 g, 1.5 eq.) and HOBT (212.5 g, 1.5 eq) in DMF, DIC (323 ml, 2.25 eq) was added. The obtained reaction mixture was added to the resin in Step B and stirred. After completion of the reaction the resin was drained and washed with DMF (2 times) and then resin was deblocked with 20% piperidine in DMF and then washed with DMF, IPA and DMF.

Step-D: Followed by sequential coupling of Fmoc-Ala-OH, Fmoc-Val-OH, Fmoc-Asn(Trt)-OH, Fmoc-Val-OH similar to the procedure described in step-C.

Step E: To a solution of Fmoc-Cys(acm)-OH (572 g, 1.5 eq.) and HOBT (212.5 g, 1.5 eq) in DMF, DIC (323 ml, 2.25 eq) was added. The obtained reaction mixture was added to the resin in Step D and stirred. After completion of the reaction, the resin was drained and washed with DMF (2 times) DCM (2 times) and MTBE (2 times). It was isolated and dried to give FMOC-Cys(Acm)-Val-Asn(Trt)-Val-Ala-Cys (Trt)-Thr(otbu)-2CTC Resin. Yield: 2.17 kg.

Step F: Selective cleavage of 2-chloro trityl resin from the Fmoc-Cys(acm)-Val-Asn(Trt)-Val-Ala-Cys(Trt)-Thr(otbu)-2CTC Resin was performed with a mixture 1% TFA in dichloromethane and then above peptidyl resin was taken in SPPS reactor and treated with a solution of 1% TFA in DCM and drained. The filtrate was immediately neutralized with precooled saturated NaHCO₃Solution to precipitate the product. The same process was repeated 3 more times and dried to obtain off-white solid. The obtained solid was further purified by treating with MTBE (2 ml/g of product) to give Fmoc-Cys(Acm)-Val-Asn(Trt)-Val-Ala-Cys(Trt)-Thr(tbu)-OH. Yield: 1133 gm; Purity: 94.29%.

Example-3: Synthesis of Boc-Asn(Xan)-Asp(Otbu)-Glu(Otbu)-Cys(Trt)-Glu(Otbu)-Leu-2CTC (Fragment D) (SEQ ID NO 4)

Step A: CTC resin (445 gm) was taken in a SPPS reactor, 4.45 L of dry dichloromethane was added and allowed it to swell for 20 min and drained.

Step B: A solution of Fmoc-Leu-OH (525 gm, 2 eq) and DIEA (388.6 ml, 3 eq) in dry dichloromethane (2.22 L) was added to the resin at step A and stirred at room temperature and drained.

The resin was then capped with DIEA (1%) solution in DCM: methanol (1:1)). Thereafter, washed the resin with one bed volume of DMF (2 times), DCM (2 times) and MTBE (2 times), isolated and dried. Yield: 700 gm.

The above resin was deblocked with 20% piperidine in DMF for 10 and 15 minutes and washed with of DMF (2 times), IPA (2 times) and DMF (2 times).

Step C: To a solution of Fmoc-Glu(Otbu)-OH (553 gm, 2.0 eq.) and HOBT (200.5 gm, 2.0 eq) in DMF, DIC (305 ml, 3.0 eq) was added. It was added to the resin in Step B. After completion of the reaction, the resin was drained and washed with DMF.

The above resin was deblocked with 20% piperidine in DMF for 10 and 15 minutes and washed with of DMF (2 times), IPA (2 times) and DMF (2 times).

Step D: Sequential coupling of Fmoc-Cys(Trt)-OH, Fmoc-Glu(Otbu)-OH, Fmoc-Asp(Otbu)-OH, Fmoc-Asp (Otbu)-OH similar to the procedure of step-C.

Step-E: To a solution of Boc-Asn(xan)-OH (537 gm, 2.0 eq.) and HOBT (200.5 gm, 2.0 eq) in DMF, DIC (305 ml, 3.0 eq) were added and stirred. It was added to the resin in Step F and stirred. After completion of the reaction, the resin was drained and washed with DMF (2 times), DCM (2 times) and MTBE (2 times). It was isolated and dried to give Boc-Asn(Xan)-Asp(Otbu)-Glu(Otbu)-Cys(Trt)-Glu(Otbu)-Leu-2CTC resin. Yield: 1.37 kg.

Step H: Selective cleavage of 2-chloro trityl resin from the Boc-Asn(Xan)-Asp(Otbu)-Glu(Otbu)-Cys(Trt)-Glu(Otbu)-Leu-2CTC resin was performed with a mixture 1% TFA in dichloromethane.

The above peptidyl resin was taken in SPPS reactor and treated with a solution of 1% TFA in DCM. The filtrate was neutralized with precooled saturated NaHCO₃ solution. The same process was repeated 3 more times, the collected organic solution was washed with water, dried with sodium sulphate and evaporated to obtain off-white solid. The obtained solid was further purified by treating with MTBE (2 ml/g of product) to give Boc-Asn(Xan)-Asp(Otbu)-Glu (Otbu)-Cys(Trt)-Glu(Otbu)-Leu-OH. Yield: 720 g; Purity: 90.74%.

Example 4: Synthesis of H-Cys(Acm)-Val-Asn (Trt)-Val-Ala-Cys(Trt)-Thr(tbu)-Gly-Cys(Acm)-Leu-Otbu (Fragment C) (SEQ ID NO 3)

Fmoc-Cys(Acm)-Val-Asn(Trt)-Val-Ala-Cys(Trt)-Thr (tbu)-OH (Fragment-A) (500.0 g, 1.0 eq) was taken in a round bottom flask containing DMF (2.5 L). H-Gly-Cys (Acm)-Leu-Otbu (Fragment B) (209 g, 1.5 eq) was added to the reaction mass and cooled to −10 to ~15° C. HOAT (50 g, 1.1 eq) and HATU (151.75 g, 1.2 eq) were added to reaction mass and then DIPEA (116 ml, 2 eq) was added drop wise while stirring at −10 to ~15° C. After completion of the reaction, methanol (15.0 L) was added to the above reaction mass (solid formation was observed), then pH of the reaction mixture was adjusted with 1N HCl up to pH 3, stirred for one hour, filtered and dried to give decapeptide. Yield: 700 g.

The above obtained decapeptide (700 g, 1.0 eq) was taken in a round bottom flask containing DMF (4.2 L) and cooled the solution to 5-10° C. Tertiary butyl amine (77.30 ml 2.0 eq) was added and stirred the reaction mass for 15 min at 5-10° C. and then stirred at R. T. After completion of the reaction, methanol (25.20 L) was added to precipitate the product. The obtained solid was filtered and dried to give NH₂-Cys(Acm)-Val-Asn(Trt)-Val-Ala-Cys(Trt)-Thr(otbu)-Gly-Cys(Acm)-Lue-Otbu. Yield: 437 g; HPLC purity: ~97%

Example 5: Synthesis of Boc-Asn(Xan)-Asp(Otbu)-Glu(Otbu)-Cys(Trt)-Glu(Otbu)-Leu-Cys(Acm)-Val-Asn(Trt)-Val-Ala-Cys(Trt)-Thr(otbu)-Gly-Cys (Acm)-Leu-Otbu. (SEQ ID NO 5)

NH₂-Cys(Acm)-Val-Asn(Trt)-Val-Ala-Cys(Trt)-Thr (otbu)-Gly-Cys-(Acm)-Lue-Otbu, (435.0 g, 1.0 eq) and Boc-Asn(Xan)-Asp(Otbu)-Glu(Otbu)-Cys(Trt)-Glu(Otbu)-Leu-OH (Fragment D), (365.0 g, 0.9 eq) were taken in a round bottom flask containing DMF (2.61 L). The solution obtained was cooled to −10 to ~15° C. and then HOAT (42.0 g, 1.2 eq) and HATU (118 g, 1.2 eq) were added. DIPEA (90 ml, 2.0 eq) was added to the reaction mass and stirred at −10 to ~15° C. Methanol (13.0 L) was added to the above reaction mass to precipitate the product. The obtained solid was filtered and dried to give Boc-Asn(Xan)-Asp(Otbu)-Glu (Otbu)-Cys(Trt)-Glu(Otbu)-Leu-Cys(Acm)-Val-Asn(Trt)-Val-Ala-Cys(Trt)-Thr(otbu)-Gly-Cys(Acm)-Leu-Otbu as off-white solid. Yield: 750 g.

Example 6: Synthesis of H-Asn-Asp-Glu-Cys-Glu-Leu-Cys(Acm)-Val-Asn-Val-Ala-Cys-Thr-Gly-Cys (Acm)-Leu-OH. (SEQ ID NO 6)

Protected peptide (500.0 g) obtained in example 5 was treated with a pre-cooled solution of 84% TFA (4200 ml), 5% TIPS (250 ml), 5% H₂O (250 ml), 5% DTT (250 gm), 1% DMS (50 ml) for 2 hrs at R. T. The product was precipitated by the addition of reaction mass to the pre-cooled MTBE, filtered the product under nitrogen and washed with MTBE and dried. Yield: 310.0 g; Purity: 73%.

Example 7: Preparation of Crude Plecanatide

Linear 1-16 peptide obtained from example 6 was dissolved in degassed 0.015 M ammonium hydroxide solution at a concentration of 1 g/0.75 L, pH was adjusted between 8.5 to 9.0 by using ammonia solution. After dissolution of compound, $H_2O_2$ (200 µl/g) was added. After completion of oxidation, the pH was adjusted between 3 to 4 by IN HCl to obtain mono cyclized 1-16 peptide solution and then solution was treated with 5% iodine in acetonitrile, till the yellow color persist. The reaction mixture with excess of iodine was quenched with 0.1M aqueous ascorbic acid solution and the pH was adjusted between 6.5 and 7 by using ammonia solution. The solution was filtered through 2.4 micron. The obtained filtrate was used as such for next stage purification.

Example 8: Purification of Plecanatide

Stage 1: Crude Plecanatide solution obtained from example 7 was purified on preparative HPLC, column was packed with reverse phase C18 hybrid silica using Tris HCl pH 7 (as buffer A) and 100% acetonitrile (as buffer B). The fractions were collected and purity of fractions were monitored by analytical HPLC. Fractions containing>94% pure Plecanatide were pooled as main pool; and fractions not meeting the pooling criteria were re-processed in a similar manner.

Stage 2: The main pool obtained from stage 1 purification were diluted with equal amount of purified water and re-purified on preparative HPLC, column was packed with reverse phase C18 hybrid silica using Tris HCl PH 7 (as buffer A) and 100% acetonitrile (as buffer B). The fractions were collected and purity of fractions were monitored by analytical HPLC. Fractions containing>98.5% pure Plecanatide were pooled as main pool for desalting. (OR)

The main pool obtained from stage-1 purification were diluted with equal amount of purified water and re-purified on preparative HPLC, column was packed with reverse phase C18 hybrid silica using TEAP (as buffer A) and acetonitrile (as buffer B). The fractions were collected and purity of fractions were monitored by analytical HPLC. Fractions containing>98.5% pure Plecanatide were pooled as main pool for desalting.

Example 9: De-Salting and Lyophilization

The main pool obtained from the purification were diluted with equal amount of purified water and loaded on preparative HPLC, column was packed with reverse phase C18 hybrid silica.

De-salting was done by passing 5 void volume of 0.1% acetic acid in purified water fallowed by elution of product from the column by using 30% acetonitrile (HPLC grade) in purified water containing 0.1% acetic acid. The fractions were collected and purity of fractions were monitored by analytical HPLC.

The fractions containing pure Plecanatide (>98.5%) were pooled; the organic modifier was removed under reduced pressure and filtered through 0.2 micron filter. The resulting peptide solution was freeze-dried to isolate Plecanatide. After completion of lyophilization cycle, the compound was unloaded and dissolved in purified water at a concentration Of 70 g/L, filtered through 0.2 micron filter. The resulting peptide solution was freeze-dried to obtain white solid lyophilized powder as Plecanatide. Purity: 99.1%

Example 10: Preparation of Mono Cyclized Plecanatide

Linear 1-16 peptide obtained from example 6 was dissolved in degassed 0.015 M ammonium hydroxide solution at a concentration of 1 g/0.75 L, the pH was adjusted between 8.5 to 9.0 by using ammonia solution. After dissolution of compound, $H_2O_2$ (200 µl/g) was added and stirred for 30 minutes. The progress of oxidation was monitored by analytical reverse phase HPLC & Ellman's test. After completion of oxidation, the pH was adjusted between 6.5 and 7 by using IN HCl to obtain mono cyclized 1-16 peptide solution.

Example 11: Purification of Mono Cyclized Plecanatide

Mono cyclized solution obtained from example 10 was purified on preparative HPLC, column packed with reverse phase C18 hybrid silica using Tris HCl PH 7 (as buffer A) and 100% acetonitrile (as buffer B). The fractions were collected and purity were monitored by analytical HPLC. Fractions containing>95% pure Plecanatide were pooled as main pool; and fractions not meeting the pooling criteria were re-processed in a similar manner.

Example 12: Preparation of Crude Plecanatide

The resultant purified solution was diluted with equal amount of water, adjusted pH 3.5 with 1N HCl and treated with 5% iodine in acetonitrile, till the yellow color persist and the reaction mass was stirred for two hours.

The completion of oxidation was monitored by analytical reverse phase HPLC; quenched the excess iodine with 0.1 M aqueous ascorbic acid solution and then pH was adjusted between 6.5 and 7 by using ammonia solution. The solution was filtered through 2.4 micron filter and used as such for next stage purification.

Example 13: Purification of Plecanatide

The main pool obtained from stage 1 purification were purified on preparative HPLC, column was packed with reverse phase C18 hybrid silica using Tris HCl pH 7 (buffer A) and 100% acetonitrile (buffer B). The fractions were collected and purity of fractions were monitored by analytical HPLC. Fractions containing>98.5% pure Plecanatide were pooled as main pool for desalting. (OR) The main pool obtained from stage 1 purification further purified on preparative HPLC, the column was packed with reverse phase C18 hybrid silica using TEAP (as buffer A) and acetonitrile (as buffer B). Fractions containing>98.5% pure Plecanatide were pooled as main pool for desalting.

Example 14: De-Salting and Lyophilization

The main pool obtained from the purification were diluted with equal amount of purified water and loaded on preparative HPLC, column packed with reverse phase C18 hybrid silica.

De-salting was done by passing 5 void volume of 0.1% acetic acid in purified water fallowed by elution of product from the column by using 30% acetonitrile (HPLC grade) in purified water containing 0.1% acetic acid. The fractions were collected and purity of fractions were monitored by analytical HPLC. The fractions containing pure Plecanatide (>98.5%) were pooled; the organic modifier was removed under reduced pressure and filtered through 0.2 micron filter. The resulting peptide solution was freeze-dried to isolate Plecanatide.

After completion of lyophilization cycle, unload the compound and dissolve in purified water at a concentration Of 70 g/L, filtered through 0.2 micron filter. The resulting peptide solution was freeze-dried to obtain white solid lyophilized powder as Plecanatide.

Purity: 99% by HPLC.

---

We claim:

1. A process for the preparation of Plecanatide of Formula I (SEQ ID NO 1):

Formula-I

H-Asn-Asp-Glu-Cys-Glu-Leu-Cys-Val-Asn-Val-Ala-Cys-Thr-Gly-Cys-Leu-OH which comprises the following steps:

a) preparing peptide Fragment A (SEQ ID NO 2), Fragment B and Fragment D (SEQ ID NO 4) separately:

b) coupling of Fragment A (SEQ ID NO 2) with Fragment B in presence of coupling agent and solvent, followed by amino deprotection to provide Fragment C (SEQ ID NO 3);

Y-Cys(Z)-Val-Asn(Y)-Val-Ala-Cys(Z)-Thr(X)-OH   Fragment A (SEQ ID NO 2)

| H-Gly-Cys(Z)-Lue(X)  Fragment B
↓

H-Cys(Z)-Val-Asn(Y)-Val-Ala-Cys(Z)-Thr(X)-Gly-Cys(Z)-Lue(X)  Fragment C (SEQ ID NO 3)

Wherein, X represents carboxyl or hydroxy protecting group;

Y represents amino protecting group; and

Z represents thiol protecting group, c) coupling of the Fragment C (SEQ ID NO 3) with Fragment D (SEQ ID NO 4);

(SEQ ID NO 4)
```
Y-Asn(Y)-Asp(X)-Glu(X)-Cys(Z)-Glu(X)-Lue-OH
Faragment D
``` in presence of coupling agent and solvent to provide protected linear peptide of SEQ ID NO 5:

(SEQ ID NO 5)
```
H-Asn(Y)-Asp(X)-Glu(X)-Cys(Z)-Glu(X)-Lue-Cys(Z)-

Val-Asn(Y)-Val-Ala-Cys(Z)-Thr(X)-Gly-Cys(Z)-

Lue(X)

Protected linear peptide
``` d) deprotecting the protected linear peptide of SEQ ID NO. 5 using deblocking cocktail mixture to obtain linear 1-16 peptide (SEQ ID NO 6); and (SEQ ID NO 6)
```
H-Asn-Asp-Glu-Cys-Glu-Lue-Cys(Z)-Val-Asn-Val-Ala- Cys-Thr-Gly-Cys(Z)-Lue-OH 1-16 linear peptide
``` e) oxidizing the linear 1-16 peptide using oxidizing agent to obtain crude Plecanatide; and f) purification of crude plecanatide using preparative HPLC using Tris hydrochloride or Triethylammonium phosphate to obtain pure plecanatide of formula I (SEQ ID NO 1).

2. The process as claimed in claim 1, wherein the process to prepare Fragments A and D involves solid phase synthesis, and process to prepare Fragment-B involves solution phase synthesis.

3. The process as claimed in claim 1, wherein the X represents carboxyl or hydroxy protecting group comprises Benzyl (Bzl), tert-butyl (tBu, trityl_(Trt), tetrahydropyranyl (THP), 2,5-dichlorobenzyl (Dcb), 2,6-dichlorobenzyl (2,6-C12Bzl) and cyclohexyl (cHx);

the Y represents amino protecting group comprises Xanthyl (Xan), fluorenylmethoxycarbonyl (Fmoc), benzyloxycarbonyl (Cbz), Trityl (Trt); and the Z represents thiol protecting comprises acetamidomethyl (Acm), Trityl (Trt), benzyl (Bzl), tert-butyl (tBu), tert-butylthio (tButhio), 4-methoxybenzyl (pMeoBzl), and monomethoxytrityl (Mmt).

4. The process as claimed in claim 1, wherein the coupling reagent is HATU O-(7-Azabenzotriazol-1-yl)-1,1,3,3-tetramethyluronium hexafluorophosphate (HATU).

5. The process as claimed in claim 1, wherein the amino deprotection in step a (b) is carried out with a tertiary-butylamine in presence of DMF.

6. The process as claimed in claim 1, wherein the deprotection of step (ed) is conducted in presence of cocktail mixture comprising Trifluoroacetic acid (TFA): Triisopropyl silane (TIPS): Dithiothreitol (DTT): water: Dimethyl sulfide (DMS) or Trifluoroacetic acid_(TFA): Triisopropyl silane (TIS): Dimethyl sulfide (DMS).

7. The process as claimed in claim 6, wherein the cocktail is 84% TFA: 5% TIPS: 5% $H_2O$: (5% DTT or 5% DMS).

8. The process as claimed in claim 1, wherein the oxidation is conducted with oxidizing agent comprises $H_2O_2$.

9. The process as claimed in claim 1, wherein the Fragment A (SEQ ID NO 2), is Fmoc-Cys(Acm)-Val-Asn(Trt)-Val-Ala-Cys(Trt)-Thr(tBu)-OH, the Fragment B is H-Gly-Cys(Acm)-Leu-OtBu, the Fragment C (SEQ ID NO 3) is H-Cys(Acm)-Val-Asn(Trt)-Val-Ala-Cys(Trt)-Thr(tBu)-Gly-Cys(Acm)-Leu-OtBu and the Fragment D (SEQ ID NO 4) is Boc-Asn(Xan)-Asp(OtBu)-Glu(OtBu)-Cys(Trt)-Glu (OtBu)-Leu-OH.

\*    \*    \*    \*    \*

```
                                  SEQUENCE LISTING

<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: Synthesized
<220> FEATURE:
<221> NAME/KEY: DISULFID
<222> LOCATION: (4)..(12)
<220> FEATURE:
<221> NAME/KEY: DISULFID
<222> LOCATION: (7)..(15)

<400> SEQUENCE: 1

Asn Asp Glu Cys Glu Leu Cys Val Asn Val Ala Cys Thr Gly Cys Leu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Cys linked to protecting group
<220> FEATURE:
<221> NAME/KEY: MISC_FEATURE
<222> LOCATION: (3)..(3)
<223> OTHER INFORMATION: Asn linked to protecting group
<220> FEATURE:
<221> NAME/KEY: MISC_FEATURE
<222> LOCATION: (6)..(6)
<223> OTHER INFORMATION: Cys linked to protecting group
<220> FEATURE:
<221> NAME/KEY: MISC_FEATURE
<222> LOCATION: (7)..(7)
<223> OTHER INFORMATION: Thr  linked to protecting group

<400> SEQUENCE: 2

Cys Val Asn Val Ala Cys Thr
1               5

<210> SEQ ID NO 3
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Cys linked to protecting group
<220> FEATURE:
<221> NAME/KEY: MISC_FEATURE
<222> LOCATION: (3)..(3)
<223> OTHER INFORMATION: Asn linked to protecting group
<220> FEATURE:
<221> NAME/KEY: MISC_FEATURE
<222> LOCATION: (6)..(6)
<223> OTHER INFORMATION: Cys linked to protecting group
<220> FEATURE:
<221> NAME/KEY: MISC_FEATURE
<222> LOCATION: (7)..(7)
<223> OTHER INFORMATION: Thr linked to protecting group
```

```
<220> FEATURE:
<221> NAME/KEY: MISC_FEATURE
<222> LOCATION: (9)..(9)
<223> OTHER INFORMATION: Cys linked to protecting group

<400> SEQUENCE: 3

Cys Val Asn Val Ala Cys Thr Gly Cys Leu
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Asn linked to protecting group
<220> FEATURE:
<221> NAME/KEY: MISC_FEATURE
<222> LOCATION: (2)..(2)
<223> OTHER INFORMATION: Asp linked to protecting group
<220> FEATURE:
<221> NAME/KEY: MISC_FEATURE
<222> LOCATION: (3)..(3)
<223> OTHER INFORMATION: Glu linked to protecting group
<220> FEATURE:
<221> NAME/KEY: MISC_FEATURE
<222> LOCATION: (4)..(4)
<223> OTHER INFORMATION: Cys linked to protecting group
<220> FEATURE:
<221> NAME/KEY: MISC_FEATURE
<222> LOCATION: (5)..(5)
<223> OTHER INFORMATION: Glu linked to protecting group

<400> SEQUENCE: 4

Asn Asp Glu Cys Glu Leu
1               5

<210> SEQ ID NO 5
<211> LENGTH: 16
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Asn linked to protecting group
<220> FEATURE:
<221> NAME/KEY: MISC_FEATURE
<222> LOCATION: (2)..(2)
<223> OTHER INFORMATION: Asp linked to protecting group
<220> FEATURE:
<221> NAME/KEY: MISC_FEATURE
<222> LOCATION: (3)..(3)
<223> OTHER INFORMATION: Glu linked to protecting group
<220> FEATURE:
<221> NAME/KEY: MISC_FEATURE
<222> LOCATION: (4)..(4)
<223> OTHER INFORMATION: Cys linked to protecting group
<220> FEATURE:
<221> NAME/KEY: MISC_FEATURE
<222> LOCATION: (5)..(5)
<223> OTHER INFORMATION: Glu linked to protecting group
<220> FEATURE:
<221> NAME/KEY: MISC_FEATURE
<222> LOCATION: (7)..(7)
<223> OTHER INFORMATION: Cys linked to protecting group
<220> FEATURE:
<221> NAME/KEY: MISC_FEATURE
<222> LOCATION: (9)..(9)
<223> OTHER INFORMATION: Asn linked to protecting group
<220> FEATURE:
```

-continued

```
<221> NAME/KEY: MISC_FEATURE
<222> LOCATION: (12)..(12)
<223> OTHER INFORMATION: Cys linked to protecting group
<220> FEATURE:
<221> NAME/KEY: MISC_FEATURE
<222> LOCATION: (13)..(13)
<223> OTHER INFORMATION: Thr linked to protecting group
<220> FEATURE:
<221> NAME/KEY: MISC_FEATURE
<222> LOCATION: (15)..(15)
<223> OTHER INFORMATION: Cys linked to protecting group
<220> FEATURE:
<221> NAME/KEY: MISC_FEATURE
<222> LOCATION: (16)..(16)
<223> OTHER INFORMATION: Leu linked to protecting group

<400> SEQUENCE: 5

Asn Asp Glu Cys Glu Leu Cys Val Asn Val Ala Cys Thr Gly Cys Leu
1               5                   10              15

<210> SEQ ID NO 6
<211> LENGTH: 16
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (7)..(7)
<223> OTHER INFORMATION: Cys linked to protecting group
<220> FEATURE:
<221> NAME/KEY: MISC_FEATURE
<222> LOCATION: (15)..(15)
<223> OTHER INFORMATION: Cys linked to protecting group

<400> SEQUENCE: 6

Asn Asp Glu Cys Glu Leu Cys Val Asn Val Ala Cys Thr Gly Cys Leu
1               5                   10              15
```